United States Patent
Ronaghi et al.

(10) Patent No.: US 7,622,281 B2
(45) Date of Patent: Nov. 24, 2009

(54) METHODS AND COMPOSITIONS FOR CLONAL AMPLIFICATION OF NUCLEIC ACID

(75) Inventors: Mostafa Ronaghi, Palo Alto, CA (US); Foad Mashayekhi, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 244 days.

(21) Appl. No.: 11/134,683

(22) Filed: May 19, 2005

(65) Prior Publication Data

US 2006/0008824 A1 Jan. 12, 2006

Related U.S. Application Data

(60) Provisional application No. 60/573,719, filed on May 20, 2004.

(51) Int. Cl.
*C12P 19/34* (2006.01)
*C12Q 1/68* (2006.01)
*C07H 21/02* (2006.01)
*C07H 21/04* (2006.01)

(52) U.S. Cl. .................. 435/91.2; 435/6; 536/23.1; 536/24.3

(58) Field of Classification Search ............ None
See application file for complete search history.

(56) References Cited

U.S. PATENT DOCUMENTS

| | | | |
|---|---|---|---|
| 4,971,903 A | 11/1990 | Hyman et al. |
| 5,002,867 A | 3/1991 | Macevicz |
| 5,093,245 A | 3/1992 | Keith et al. |
| 5,185,243 A | 2/1993 | Ullman et al. |
| 5,302,509 A | 4/1994 | Cheeseman |
| 5,503,980 A | 4/1996 | Cantor |
| 5,547,839 A | 8/1996 | Dower et al. |
| 5,604,097 A | 2/1997 | Brenner |
| 5,639,603 A | 6/1997 | Dower et al. |
| 5,763,175 A | 6/1998 | Brenner |
| 5,780,231 A | 7/1998 | Brenner |
| 5,795,714 A | 8/1998 | Cantor et al. |
| 5,795,716 A | 8/1998 | Chee et al. |
| 5,846,719 A | 12/1998 | Brenner |
| 5,853,989 A | 12/1998 | Jeffreys et al. |
| 5,854,033 A | 12/1998 | Lizardi |
| 5,900,481 A | 5/1999 | Lough et al. |

(Continued)

FOREIGN PATENT DOCUMENTS

EP  0799897  10/1997

(Continued)

OTHER PUBLICATIONS

Shizuya, H. et al., Keio J. Med., vol. 50, pp. 26-30 (2001).*

(Continued)

*Primary Examiner*—Teresa E Strzelecka
(74) *Attorney, Agent, or Firm*—David J. Aston; Peters Verny, LLP (57) ABSTRACT

Described herein are methods and compositions relating to amplifying nucleic acid. In certain embodiments, the invention provides methods for labeling and amplifying a nucleic acid molecule.

19 Claims, 2 Drawing Sheets

U.S. PATENT DOCUMENTS

| | | | |
|---|---|---|---|
| 5,902,723 | A | 5/1999 | Dower et al. |
| 5,935,793 | A | 8/1999 | Wong et al. |
| 5,942,391 | A | 8/1999 | Zhang et al. |
| 5,981,176 | A | 11/1999 | Wallace |
| 6,013,445 | A | 1/2000 | Albrecht |
| 6,023,540 | A | 2/2000 | Walt et al. |
| 6,027,889 | A | 2/2000 | Barany et al. |
| 6,060,245 | A | 5/2000 | Sorge |
| 6,107,023 | A | 8/2000 | Reyes et al. |
| 6,143,495 | A | 11/2000 | Lizardi et al. |
| 6,172,218 | B1 | 1/2001 | Brenner |
| 6,210,891 | B1 | 4/2001 | Nyren et al. |
| 6,225,064 | B1 | 5/2001 | Uematsu et al. |
| 6,258,568 | B1 | 7/2001 | Nyren |
| 6,268,148 | B1 | 7/2001 | Barany et al. |
| 6,274,320 | B1 | 8/2001 | Rothberg et al. |
| 6,280,935 | B1 | 8/2001 | Macevicz |
| 6,306,607 | B2 | 10/2001 | Williams |
| 6,327,410 | B1 | 12/2001 | Walt et al. |
| 6,383,754 | B1 * | 5/2002 | Kaufman et al. ............... 435/6 |
| 6,406,848 | B1 | 6/2002 | Bridgham et al. |
| 6,458,530 | B1 | 10/2002 | Morris et al. |
| 6,534,293 | B1 | 3/2003 | Barany et al. |
| 6,627,402 | B2 | 9/2003 | Wallace |
| 6,812,005 | B2 | 11/2004 | Fan et al. |
| 6,828,100 | B1 | 12/2004 | Ronaghi |
| 6,890,741 | B2 | 5/2005 | Fan et al. |
| 6,913,884 | B2 | 7/2005 | Stuelpnagel et al. |
| RE39,793 | E | 8/2007 | Brenner |
| 7,323,305 | B2 | 1/2008 | Leamon et al. |
| 7,399,846 | B2 | 7/2008 | Southern et al. |
| 2002/0132221 | A1 | 9/2002 | Chee et al. |
| 2003/0068629 | A1 | 4/2003 | Rothberg et al. |
| 2003/0108867 | A1 | 6/2003 | Chee |
| 2003/0108900 | A1 | 6/2003 | Oliphant |
| 2003/0162217 | A1 | 8/2003 | Rothberg et al. |
| 2003/0170684 | A1 | 9/2003 | Fan |
| 2003/0211489 | A1 | 11/2003 | Shen |
| 2004/0101835 | A1 | 5/2004 | Willis et al. |
| 2004/0197793 | A1 | 10/2004 | Hassibi et al. |
| 2005/0130173 | A1 | 6/2005 | Leamon et al. |

FOREIGN PATENT DOCUMENTS

| | | |
|---|---|---|
| GB | 2156074 | 10/1985 |
| WO | WO-89/10977 | 11/1989 |
| WO | 9302360 | 2/1993 |
| WO | 9323564 | 11/1993 |
| WO | 9630392 | 10/1996 |
| WO | 9603212 | 11/1996 |
| WO | 9746704 | 12/1997 |
| WO | 9813523 | 4/1998 |
| WO | 9828440 | 7/1998 |
| WO | 9853300 | 11/1998 |
| WO | 0058516 | 10/2000 |
| WO | WO 02/061143 | 8/2002 |

OTHER PUBLICATIONS

Dorre, K. et al., Bioimaging, vol. 5, pp. 139-152 (1997).*

Vogelstein, B. et al., PNAS USA, vol. 96, pp. 9236-9241 (1999).*

Bains et al., "A novel method for nucleic acid sequence determination," J Theor Biol. 135(3):303-7, (1998).

Batzoglou et al., "Arachne: a whole-genome shotgun assembler," Genome Res., 12(1):177-89, (2002).

Batzoglou et al., "Human and mouse gene structure: comparative analysis and application to exon prediction," Genome Res., 10(7):950-8, (2000).

Braslavsky et al., "Sequence information can be obtained from single DNA molecules," PNAS, 100(7):3960-3964, (2003).

Brenner et al., "Gene expression analysis by massively parallel signature sequencing (MPSS) on microbead arrays," Nat Biotechnol., 18(6):630-4, (2000).

Brenner et al., "In vitro cloning of complex mixtures of DNA on microbeads: Physical separation of differentially expressed cDNAs," PNAS, 97(4):1665-1670, (2000).

Collins et al., "The Human Genome Project: Lessons from Large-Scale Biology," Science, 300:286-290, (2003).

Deamer et al., "Characterization of nucleic acids by nanopore analysis," Acc Chem Res., 35(10):817-25, (2002).

Deamer et al., "Nanopores and nucleic acids: prospects for ultrarapid sequencing," Trends Biotechnol., 18(4):147-51, (2000).

Dressman, et al., "Transforming single DNA molecules into fluorescent magnetic particles for detection and enumeration of genetic variations," PNAS, 100(15):8817-8822, (2003).

Drmanac et al., "Accurate sequencing by hybridization for DNA diagnostics and individual genomics," Nat Biotechnol., 16(1):54-8, (1998).

Drmanac et al., "DNA sequencing by hybridization with arrays of samples or probes," Methods Mol Biol., 170:173-9 (2001).

Elahi et al., "Global Genetic Analysis," Jour. of Biochem. and Mol. Biol., 37(1):11-27, (2004).

Emrich et al., "Microfabricated 384-lane capillary array electrophoresis bioanalyzer for ultrahigh-throughput genetic analysis," Anal Chem., 74(19):5076-83, (2002).

Fodor et al., "Light-Directed, Spatially Addressable Parallel Chemical Synthesis," Science, 251:767-773, (1991).

Jaffe et al., "Whole-genome sequence assembly for mammalian genomes: Arachne 2," Res., 13(1):91-6, (2003).

Koutny et al., "Eight hundred-base sequencing in a microfabricated electrophoretic device," Anal Chem., 72(14):3388-91, (2000).

Leamon et al., "A massively parallel PicoTiterPlate based platform for discrete picoliter-scale polymerase chain reactions," Electrophoresis, 24(21):3769-77, (2003).

Levene et al., "Zero-Mode Waveguides for Single-Molecule Analysis at High Concentrations," Science, 299:682-686, (2003).

Li et al., "DNA molecules and configurations in a solid-state nanopore microscope," Nat Mater., 2(9):611-5, (2003).

Lipshutz et al., "Using oligonucleotide probe arrays to access genetic diversity," Biotechniques.19(3):442-7, (1995).

Metzker et al., "Termination of DNA synthesis by novel 3'-modified-deoxyribonucleoside 5'- triphosphates," Nucleic Acids Res. 22(20):4259-67, (1994).

Mitra et al., "In situ localized amplification and contact replication of many individual DNA molecules," Nucleic Acids Res., 27(24):e34, (1999).

Mitra, et al., "Digital genotyping and haplotyping with polymerase colonies," PNAS, 100(10):5926-5931, (2003).

Paegel et al., "Microfluidic devices for DNA sequencing: sample preparation and electrophoretic analysis," Curr Opin Biotechnol., 14(1):42-50, (2003).

Patil, et al., "Blocks of Limited Haplotype Diversity Revealed by High-Resolution Scanning of Human Chromosome 21," Science, 294:1719-1723, (2001).

Ronaghi et al., A sequencing method based on real-time pyrophosphate., Science, 281(5375):363, 365, (1998).

Ronaghi et al., "Analyses of secondary structures in DNA by pyrosequencing," Anal Biochem., 267(1):65-71, (1999).

Ronaghi et al., "Pyrosequencing for microbial typing," J Chromatogr B Analyt Technol Biomed Life Sci., 782(1-2):67-72, (2002).

Ronaghi et al., "Real-time DNA sequencing using detection of pyrophosphate release," Anal Biochem., 242(1):84-9, (1996).

Ronaghi, M. "Pyrosequencing sheds light on DNA sequencing," Genome Res., 11(1):3-11, (2001).

Ronaghi, M., "Pyrosequencing for SNP genotyping," Methods Mol Biol., 212:189-95, (2003).

Sanger et al., "DNA sequencing with chain-terminating inhibitors," Proc. Natl. Acad. Sci., 74(12):5463-5467, (1977).

Winters-Hilt et al., "Highly Accurate Classification of Watson-Crick Basepairs on Termini of Single DNA Molecules," Biophysical Journal, 84:967-976, (2003).

Reeves, R. E., et al., "Enzymic assay method for inorganic pyrophosphate", Anal. Biochem., 1969, vol. 28., 282-287.

Cook, et al., "A rapid Enzymatic Assay for Measurement of Inorganic Pyrophosphate in Animal Tissues", Anal. Biochem., 1978, 91:557.

Helfman, et al., "Identification of clones that encode chicken tropomyosin by direct immunological screening of a cDNA expression library", PNAS US 80, 1983, 31-35.

Nyren, p. et al., "Enzymatic method for continuous monitoring of inorganic pyrophosphate synthesis", Anal. Biochem., 1985, 151:504-509.

Kimmel, et al., "Preparation of cDNA and the Generation of cDNA Libraries: Overview", Methods in Enzymology, 1987, 152, 307-316.

Barshop, et al., "Luminescent immobilized enzyme test systems for inorganic pyrophosphate:assays using firefly luciferase and nicotinamide-mononucleotide adenylyl transferase or adenosine-5'-triphosphate sulfurylase", Anal. Biochem., 1991, 197(1) 266-272.

Hyman, E D., "A new method of sequencing DNA", Anal. Biochem, 1988, vol. 174, 423-436.

Chee, M et al., "Enzymatic multiplex DNA sequencing", Nucl. Acid Res., 1991, vol. 19, No. 12., 3301-3305.

Justesen, et al., "Spectrophotometric Pyrophosphate Assay of 2', 5'-Oligoadenylate Synthetase", Anal. Biochem., 1992, 207 (1):90-93.

Nyren, et al., "Solid Phase DNA Minisequencing by an Enzymatic Luminometric Inorganic Phyrophosphate Detection Assay", Anal Biochem., Jan. 1993; 208 (1):171-5.

Broude, et al., "Enhanced DNA sequencing by hybridization", PNAS, 1994, 91, 3072-3076.

Nyren, "Apyrase Immobilized on Paramagnetic Beads Used to Improve Detection Limits in Bioluminometric ATP monitoring", J. Biolumin Chemilumin, Jan.-Feb. 1994; 9 (1):29-34.

Nyren, et al., "Detection of Single-Base Changes Using a Bioluminometric Primer Extension Assay", Anal. Biochem., Jan. 15, 1997; 244 (2) 367-73.

Karamohamed and Nyren, et al., "Real-Time detection and quantification of adenosine triphosphate sulfurylase activity by a bioluminometric approach", Anal. Biochem., 1999, 271:81-85.

Hirschhorn, J N., "SBE Tags: An Array Based Method for Efficient Nucleotide Polymorphisms Genotyping.", PNAS, 2000, vol. 97, No. 22, 12164-12169.

Fan, "Parallel Genotyping of Human SNPs Using Generic High-density Oligonucleotide Tag Arrays", Genome Research, 2000, vol. 10, 853-860.

Ladner, et al., "Multiplex detection of hotspot mutations by rolling circle-enabled universal microarrays.", Lab. Invest: J. Tech. Meth. Path, 2001, 81:1079-1086.

Margulies, Marcel et al., "Genome Sequencing in microfabricated high-density picolitre reactors", Nature, Jul. 31, 2005, vol. 437, No. 7057, 376-380.

* cited by examiner

METHODS AND COMPOSITIONS FOR CLONAL AMPLIFICATION OF NUCLEIC ACID

RELATED APPLICATION

This application claims the benefit of the filing date of U.S. Provisional Application No. 60/573,719 filed May 20, 2004 and entitled "Methods and Compositions for Clonal Amplification of Nucleic Acid" by Mostafa Ronaghi and Foad Mashayekhi. The entire teachings of the referenced Provisional Application are incorporated herein by reference.

FUNDING

Work described herein was funded, in whole or in part, by National Institutes of Health Grant Number 2POIHG00205. The United States government has certain rights in the invention.

BACKGROUND

The essence of biology is an understanding of all of the species and their biological mechanisms. Speciation and biological function are primarily determined by the organism's DNA sequence. The development of vastly improved DNA sequence determination for personalized medicine and ecological studies could complete the revolution initiated by the Human Genome Project.

The Human Genome Project was markedly accelerated during the last several years and was completed with blistering speed. The complete nucleotide sequence of the human genome was completed in approximately 13 years (Collins et al., 2003) and the genome was published in 2003 (www-.genome.gov/11006929). There are currently over $3 \times 10^{10}$ nucleotides in public databases (www.ncbi.nlm.nih.gov/genbank/genbankstats), and genome sequences of over 185 organisms have been fully sequenced, as well as parts of the genomes of over 100,000 taxonomic species (www.integratedgenomics.com/gold).

The Human Genome Project was essentially accomplished by a reduction in the cost of DNA sequencing by three orders of magnitude. To reduce the cost by another two or three orders of magnitude, a highly integrated platform will be needed. Although the Human Genome Project took gel-based Sanger sequencing and achieved a decrease in cost and increase in throughput by over three orders of magnitude, the project was unable to develop any competitive alternative technology for genome sequencing.

Large bacterial genomes and genomes from complex organisms are often fragmented in two steps in order to simplify the assembly process. After constructing large-insert libraries, each clone is further fragmented and smaller libraries are prepared for bi-directional shotgun sequencing. Although the material cost of creating libraries is minimal, the process has proven to be laborious for large-scale genome sequencing. Therefore, alternative strategies need to be developed.

SUMMARY

The present invention provides a method of labeling and amplifying a nucleic acid molecule. In certain embodiments, the subject invention provides a method of labeling and amplifying a nucleic acid molecule, comprising attaching a unique primer to the nucleic acid molecule to be amplified and amplifying said labeled nucleic acid molecule. In certain embodiments, the unique primer is an adapter comprising a unique barcode. In additional embodiments, the unique primer is attached to the nucleic acid molecule by ligating the adapter comprising a unique barcode to the nucleic acid molecule. In further embodiments, the unique barcode comprises a unique sequence of five nucleotides. In yet other embodiments, the unique primer identifies a source of nucleic acid. In additional embodiments, the unique barcode identifies a source of nucleic acid. In certain embodiments, the source of nucleic acid is selected from the group consisting of: a BAC clone, a bacterium, and a tissue sample. In other embodiments, the labeled nucleic acid molecule is amplified by a sequencing-by-synthesis method. In certain embodiments, the labeled nucleic acid molecule is amplified by a method selected from the group consisting of: massively parallel signature sequencing, BEAM, and polony technology.

The invention additionally relates to a method of amplifying a nucleic acid molecule, comprising (a) labeling the nucleic acid molecule with a unique primer; (b) hybridizing said nucleic acid molecule to one or more anti-primers immobilized on a solid surface; (c) incubating the solid surface of (b) with polymerase and nucleotides under conditions permitting extension of said one or more anti-primers; (d) incubating the solid surface of (c) under conditions permitting denaturing of the nucleic acid molecules from the extended anti-primers; removing the supernatant; incubating the solid surface with polymerase, labeled nucleotides, and one or more oligonucleotides that hybridize to the immobilized extended anti-primers of (c), under conditions permitting extension of said hybridized oligonucleotides; and identifying said solid surfaces comprising the extended hybridized oligonucleotides; (e) immobilizing additional anti-primers on the solid surfaces of (d); and (f) incubating the solid surfaces of (e) with polymerase, nucleotides, and one or more oligonucleotides that hybridize to the immobilized anti-primers of (e), under conditions permitting extension of said hybridized oligonucleotides, wherein the nucleic acid molecule is thereby amplified. An "anti-primer" is an oligonucleotide that hybridizes to a unique primer of the subject invention. In certain embodiments, an anti-primer will be complementary, in whole or in part, to a unique primer of the subject invention. In certain embodiments, a unique primer is an adapter comprising a unique barcode. In further embodiments, the unique barcode comprises a unique sequence of five nucleotides. In additional embodiments, invention further relates to (g) sequencing the immobilized amplified nucleic acid molecules of (f). In certain embodiments of the invention, the nucleic acid molecules are sequenced by pyrosequencing. In further embodiments, the unique primer identifies a source of nucleic acid. In other embodiments, the unique barcode identifies a source of nucleic acid. In certain embodiments, the source of nucleic acid is selected from the group consisting of: a BAC clone, a bacterium, and a tissue sample. In certain embodiments, the solid surface is a bead. In certain further embodiments, the bead is selected from the group consisting of: a magnetic bead and a Sepharose bead.

The present invention additionally relates to a nucleic acid molecule attached to a solid surface and comprising a unique primer. In certain embodiments, the unique primer is an adapter that comprises a unique barcode. In further embodiments, the unique barcode comprises a unique sequence of five nucleotides. In additional embodiments, the solid surface is a bead.

In additional embodiments, the present invention relates to a solid surface comprising one or more nucleic acid molecules prepared by a method comprising: (a) labeling the nucleic acid molecule with a unique primer; (b) hybridizing said nucleic acid molecule to one or more anti-primers immobilized on a solid surface; (c) incubating the solid surface of (b) with polymerase and nucleotides under conditions permitting extension of said one or more anti-primers; (d) incubating the solid surface of (c) under conditions permitting denaturing of the nucleic acid molecules from the immobilized extended anti-primers; removing the supernatant; incubating the solid surface with polymerase, labeled nucleotides, and one or more oligonucleotides that hybridize to the extended anti-primers of (c), under conditions permitting extension of said hybridized oligonucleotides; and identifying said solid surfaces comprising the extended hybridized oligonucleotides; (e) immobilizing additional anti-primers on the solid surfaces of (d); and (f) incubating the solid surfaces of (e) with polymerase, nucleotides, and one or more oligonucleotides that hybridize to the immobilized anti-primers of (e), under conditions permitting extension of said hybridized oligonucleotides, wherein the nucleic acid molecule is thereby amplified.

In further embodiments, the present invention relates to a kit comprising: (a) a unique primer; (b) a solid surface comprising immobilized anti-primers thereon; (c) oligonucleotides that hybridize to the immobilized anti-primers of (b); and (d) instructions for amplifying a nucleic acid molecule. In certain embodiments, the unique primer of (a) is an adapter comprising a unique barcode. In additional embodiments, the unique barcode comprises a unique sequence of five nucleotides. In further embodiments, the instructions of (d) include instructions for amplifying a nucleic acid molecule according to a method comprising: (a) labeling the nucleic acid molecule with a unique primer; (b) hybridizing said nucleic acid molecule to one or more anti-primers immobilized on a solid surface; (c) incubating the solid surface of (b) with polymerase and nucleotides under conditions permitting extension of said one or more anti-primers; (d) incubating the solid surface of (c) under conditions permitting denaturing of the nucleic acid molecules from the extended anti-primers; removing the supernatant; incubating the solid surface with polymerase, labeled nucleotides, and one or more oligonucleotides that hybridize to the immobilized extended anti-primers of (c), under conditions permitting extension of said hybridized oligonucleotides; and identifying said solid surfaces comprising the extended hybridized oligonucleotides; (e) immobilizing additional anti-primers on the solid surfaces of (d); and (f) incubating the solid surfaces of (e) with polymerase, nucleotides, and one or more oligonucleotides that hybridize to the immobilized anti-primers of (e), under conditions permitting extension of said hybridized oligonucleotides, wherein the nucleic acid molecule is thereby amplified.

DETAILED DESCRIPTION OF THE INVENTION

Described herein are methods for labelling nucleic acid molecules for clonal amplification and identification. The present invention relates to labelling nucleic acid molecules with a nucleic acid barcode, which enables easy identification of the nucleic acid after amplification and sequencing of the barcoded nucleic acid molecule. The present invention also relates to barcodes, which are nucleic acid tags that may be ligated to a nucleic acid molecule that is to be amplified and, in certain embodiments, sequenced. In certain preferred embodiments, the barcodes of the present invention comprise five nucleotides, preferably in a uniquely identifiable sequence.

In certain embodiments, the subject invention relates to a nucleic acid molecule that includes an adapter. An adapter of the invention comprises nucleic acid that hybridizes to a primer, such as an immobilized primer described herein. In certain embodiments, the present invention relates to a nucleic acid molecule that includes a barcode sequence. For example, in certain embodiments, the present invention relates to a nucleic acid molecule that includes an adapter that comprises a barcode sequence. In certain further embodiments, the invention provides a distinct barcode sequence such that each member of, e.g., a Bacterial Artificial Chromosome (BAC) library, can later be identified if isolated individually or as part of an enriched population of nucleic acid molecules. For example, a BAC library may be fragmented into 1000 base pair-long DNA fragments. The fragmented genomic DNA can then be saturated with a unique barcode for ligation. Genomic DNA from one BAC will then carry a unique barcode (e.g., five nucleotides in a unique sequence) that can later be identified easily, for example, after amplification and sequencing of the genomic DNA fragment. The barcoded clonal amplification described herein can be used to facilitate the sequencing of a genome. For example, the present invention provides for easier fragment assembly of genomic DNA fragments, such as barcoded nucleic acid fragments as described herein that have been amplified and sequenced.

Genome sequencing can be divided into three steps: upstream processing including sample preparation, DNA sequencing, and fragment assembly.

Prior to sequencing, a genome is usually fragmented into smaller pieces. Viral genomes are relatively small and can often be sequenced in one step of a restriction digest. However, large bacterial genomes and genomes from complex organisms are often fragmented in two steps in order to simplify the assembly process. Genomes are currently being partially restricted with enzymes into large fragments of 100-250 kb in size and cloned into Bacterial Artificial Chromosomes (BACs) and P1-derived Artificial Chromosomes (PACs). BAC vectors are preferable for the construction of genomic libraries mostly due to their smaller vector size (about 8 kb versus about 15 kb for PACs) which has a favorable effect on the economies of clone-by-clone shotgun sequencing. After constructing these large-insert libraries, each clone is further fragmented and smaller libraries are prepared for bi-directional shotgun sequencing. Although the material cost of creating libraries is minimal, the process has proven to be laborious for large-scale genome sequencing.

An alternative strategy is subcloning the large-insert and smaller genomes onto beads, a process known as clonal amplification. This process involves chopping the DNA into small pieces and cloning the chopped DNA onto beads prior to amplification, producing a unique set of DNA on each bead. Initially, each bead will carry a single DNA molecule. After amplification, each bead will contain thousands to millions of identical copies of the DNA molecule. This amplification is important in order to achieve sufficient signal for detection.

Several techniques have been introduced and tested, most notably polony technology (Mitra and Church, 1999), BEAM by Vogelstein's group (Dressman et al., 2003), and a cloning strategy developed for massively parallel signature sequencing (MPSS) (Brenner et al., 2000b). 454 Life Sciences, which employs Pyrosequencing as a technique for genome sequencing, has used a microemulsion technique to clone and amplify (Leamon and al., 2003) unique DNA fragments onto the beads, a strategy similar to BEAMing. This technique has been used to sequence six genomes, one of which is the Adenovirus genome and has been put in public databases (Sarkis and al., 2003). All the above-mentioned methods for clonal amplification may be appropriate for sequencing-by-synthesis.

Overview of Ultra-Fast DNA Sequencing (UDS):

With the availability of the human genome sequence, increasing emphasis has been focused on technologies for genotyping or resequencing specific areas of the genome for SNP discovery. Currently, chip-based techniques have dominated this field (Elahi et al., 2004). However, it is believed that de novo sequencing will be needed to develop a deeper understanding beyond polygenic factors that contribute to human diseases. When evaluating a technology, the following parameters are usually considered: the throughput, cost per instrument, cost per base, accuracy, and read-length of individual fragments. Here, we summarize a set of UDS technologies that have the potential to offer de novo sequencing fulfilling the above-mentioned criteria although they are still in relatively early stages of development. These technologies include electrophoretic methods, sequencing-by-hybridization (SBH), sequencing-by-synthesis (SBS), massively parallel signature sequencing (MPSS), and non-enzymatic single-molecule sequencing methods.

Electrophoretic Sequencing:

The well-proven and elegant Sanger DNA sequencing method (Sanger et al., 1977), which is based on the electrophoretic separation of DNA fragments with single-base resolution, is the dominant DNA sequencing technology and has served the community for 27 years. The current cost per base is about 0.1 cents for advanced Genome Centers, however, it ranges from 5 to 20 cents per base for other laboratories. Typically, 99.99% accuracy can be achieved with as few as three raw reads covering a given nucleotide. This technology is currently being miniaturized and integrated by several groups, including the Mathies group (Enrich et al., 2002) and researchers at the Whitehead BioMEMS laboratory in collaboration with Network BioSciences (Koutny and Al., 2000; Paegel et al., 2003).

Sequencing-By-Hybridization (SBH):

SBH was proposed by several groups more than 15 years ago (Bains and Smith, 1988; Drmanac, 1998; Fodor et al., 1995; Southern, 1989). The basic principle of SBH is that differential hybridization of oligonucleotide probes can be used to decode a target DNA sequence. The most common approach involves immobilizing the DNA to be sequenced on a solid support and then performing serial hybridizations with short probe oligonucleotides (5 to 8 nucleotide long). The extent to which specific probes bind can be used to infer the unknown sequence. The strategy has been applied to both genome resequencing and de novo sequencing (Drmanac and al., 2001; Drmanac, 1998). Affymetrix and its spin-off Perlegen have used a different approach to SBH by hybridizing sample DNA to high density oligonucleotide arrays (Lipshutz and al., 1995). The current maximum density of Affymetrix arrays is about one oligonucleotide feature per 5 micron square, where each feature consists of roughly 100,000 copies of a defined 25 base pair oligonucleotide. For each base pair of a reference genome to be resequenced, there are four features on the chip. By hybridizing labeled sample DNA to the chip and determining which of the four features yields the strongest signal for each base pair in the reference sequence, a DNA sample can be rapidly resequenced. Miniaturization, bioinformatics, and the availability of a reference human genome sequence has permitted Perlegen to greatly extend this approach and develop an oligonucleotide array for resequencing human chromosome 21 (Patil et al., 2001).

SBH technology possesses a unique set of advantages and challenges. It can be used to obtain an impressive amount of sequence (>109 bases) from many distinct chromosomes. The primary challenge of SBH is the cross-hybridization of probes to incorrect targets due to repetitive elements or chance similarities. These factors render a substantial fraction of Chromosome 21 (more than 50%) inaccessible (Patil et al., 2001), and might also contribute to the 3% false-positive SNP detection rate observed in that study. It is also worth noting that SBH still requires sample preparation steps, as the relevant fraction of the genome must be PCR-amplified prior to hybridization.

Sequencing-By-Synthesis (SBS):

SBS methods generally involve enzymatic extension by polymerase through the iterative addition of nucleotides. Each nucleotide addition, called a cycle, only queries one or a few bases, but thousands or millions of features can be processed in parallel when the assay is performed in array format. These array features may be ordered or randomly dispersed. The progression of the primer strand can be monitored either by fluorescence using labeled nucleotides or enzymatically using natural nucleotides. Several groups reported on SBS using fluorescent nucleotides more than a decade ago (Metzker et al., 1994). Other groups have made advances in microfabrication and integration of SBS using fluorescent nucleotides. Most notable is the work performed by Quake's (Braslavsky et al., 2003) and Church's (Mitra et al., 2003; Mitra and Church, 1999) groups. Pyrosequencing is another SBS-based technique which was developed recently (Ronaghi, 2001; Ronaghi et al., 1996; Ronaghi et al., 1998). All of the above-mentioned SBS methods require an amplification step prior to sequencing in order to achieve the required signal fidelity.

Several groups have worked on developing single-molecule DNA sequencing techniques based on SBS, most notably Solexa (www.solexa.com), Genovoxx (www.genovoxx.de), Nanofluidics (Levene and al., 2003) (in collaboration with Craighead's group), and Helicos (Braslavsky et al., 2003) (in collaboration with Quake's group). With respect to the ease and reliability of detecting extension events, SBS methods that sequence amplified molecules have an obvious advantage over single-molecule methods.

Massively Parallel Signature Sequencing (MPSS):

This method relies on cycles of restriction digestion and ligation (Brenner et al., 2000a). In MPSS, array features are sequenced at each cycle by employing a type II restriction enzyme to cleave within a target sequence, leaving a four base-pair overhang. Sequence-specific ligation of a fluorescent linker is then used to query the identity of the overhang. The achievable 8 to 16 bp read-lengths (which involves 3 to 4 cycles) are adequate for many purposes (Brenner et al., 2000a), but not for whole-genome sequencing.

Non-Enzymatic Single-Molecule DNA Sequencing:

Another UDS single-molecule approach is nanopore sequencing (Deamer and Akeson, 2000; Deamer and Branton, 2002; Li et al., 2003). As DNA passes through a nanopore, different base-pairs obstruct the pore to varying degrees, resulting in fluctuations in the electrical conductance of the pore. The pore conductance can therefore be measured and used to infer the DNA sequence. The accuracy of base-calling ranges from 60% for single events to 99.9% for 15 events (Winters-Hilt et al., 2003). However, the method has thus far been limited to the terminal base-pairs of a specific type of hairpin. This method has a great deal of long-term potential for extraordinarily rapid sequencing with little to no sample preparation. However, it is likely that significant pore engineering will be necessary before we can achieve a single-base resolution. Rather than engineering a pore to probe single nucleotides, Visigen (www.visigenbio.com/tech.html) and Li-Cor (Williams, 2001) are attempting to engineer DNA polymerases or fluorescent nucleotides to provide real-time, base-specific signals while synthesizing DNA at its natural pace.

Pyrosequencing:

Pyrosequencing relies on the real-time detection of inorganic pyrophosphate (PPi) released on successful incorporation of nucleotides during DNA synthesis. PPi is immediately converted to adenosine triphosphate (ATP) by ATP sulfurylase, and the level of ATP generated is detected via luciferase-producing photons. Unused ATP and deoxynucleotides are washed in the three-enzyme system of Pyrosequencing (Ronaghi et al., 1996) and degraded in the four-enzyme system of Pyrosequencing (Ronaghi et al., 1998) by the nucleotide-degrading enzyme apyrase. The presence or absence of PPi, and therefore the incorporation or nonincorporation of each nucleotide added, is ultimately assessed on the basis of whether or not photons are detected.

There is a minimal time lapse between these events, and the conditions of the reaction are such that iterative addition of nucleotides and PPi detection are possible. Prior to the start of the Pyrosequencing reactions, an amplicon is generated by PCR in which one of the primers is biotinylated at its 5' terminus. The biotinylated double-stranded DNA PCR products are then linked to a solid surface coated with streptavidin and denatured. The two strands are separated, and the strand bound to the solid surface is usually used as the template. After hybridizing a sequencing primer to this strand, DNA synthesis under Pyrosequencing conditions can commence.

In Pyrosequencing, 1 pmol of DNA template molecules can generate the same number of ATP molecules per nucleotide incorporated, which, in turn, can generate more than $6 \times 10^9$ photons at a wavelength of 560 nm. This amount of light is easily detected by a photodiode, photomultiplier tube, or charge-coupled device (CCD) camera.

Experimental Design and Methods:

The procedure for the standard Pyrosequencing reaction comprises in vitro amplification, template preparation, and Pyrosequencing. For highly parallel genome sequencing the amplification step will be rate-limiting. To circumvent this rate limiting step, clonal amplification is proposed, in a step where large numbers of DNA are clonally amplified on a single bead.

The subject invention relates to a labelling strategy, which will allow multiplexing the sequencing of a large number of clones within a single chamber. This labelling step can also be applied to the strategies described above and by others (Brenner et al., 2000b; Dressman et al., 2003; Leamon and al., 2003; Mitra and Church, 1999). Described herein is a strategy to clonally amplify a unique DNA on a solid surface such as magnetic beads.

Figure 1:
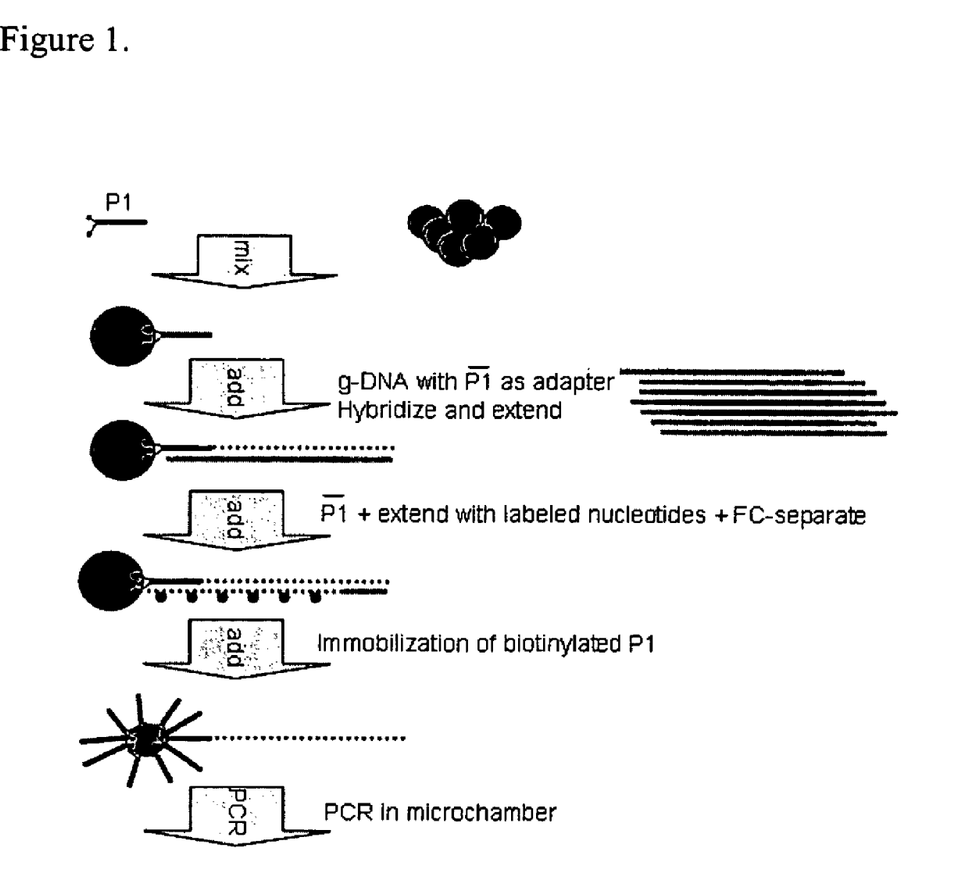
FIG. 1 is a schematic relating to barcoded clonal amplification.

Preparation of Beads Carrying Single P1 Molecule:

P1 is a 30-base long general oligonucleotide, which can be any unique sequence such as, e.g., 5'-TTTTTTTTGCAAAT-GTTATCGAGGTCCGGC (SEQ ID NO: 1), that has two biotin molecules at the 5' end. Two biotin molecules permit efficient immobilization and also allow use of a higher temperature without being detached from the streptavidin molecule (Dressman et al., 2003). The ratio of magnetic beads to P1 primers is designed to be large so that most beads that capture a primer molecule will capture exactly one. The solution will be saturated with fluorescently labeled anti-P1 (seen as P1 bar in FIG. 1), which will allow isolation of all beads carrying P1 and recycling of the remaining beads.

Preparation of Unique Adapters:

The adapters are double stranded oligonucleotides. For example, adapters will be synthesized on the order of 100 unique adapters. The coding strand of the adapter carries the same sequence as P1 followed by a unique sequence of five nucleotides (part of the oligonucleotide). For the complementary strand of the adapter, 100 different coding strands will be synthesized. Synthesis of non-coding strands starts with five unique nucleotides (complementary to the one chosen for the coding strands) followed by the complementary sequence of P1 (shown as P1 bar in FIG. 1). The 5' end of the latter strand will be phosphorylated. Both strands are mixed together in 100 different tubes to make 100 different adapters.

Preparation of Genomic DNA for Clonal Amplification:

The BAC library will be nebulized to roughly 1000 bp-long DNA fragments. The fragmented DNA from each BAC will then be end repaired and gel purification will be used to select DNA fragment sizes between 800-1200 nucleotides long. Next, the fragmented genomic DNA will be saturated with one of the unique adapters for ligation. At this step, the adapters can simply be ligated from one end (the end carrying phosphorylated 5'-end). Genomic DNA carrying adapters will be gel purified from non-ligated adapters. Now, all genomic DNA from one BAC will carry a unique barcode (a unique sequence of 5 nucleotides) that can later be identified easily in from the read.

Single Molecule Capture of Genomic DNA on Bead and Extension:

Since the beads selected previously have a single attached P1 primer, they can only capture a single DNA fragment. Therefore, we saturate the beads with denatured genomic DNA for hybridization overnight. Though there are two capture sites on each DNA fragment, at least 10 cycles of extension are performed (each cycle comprises denaturation, hybridization, and extension) with polymerase and nucleotides present; therefore, all captured DNA fragments should be extended. After these extension cycles, all the magnetic beads are isolated and washed.

Labeling of Captured DNA:

Isolated beads from the previous step will be treated with alkali to denature the DNA and then the supernatant is removed. Anti-P1 is added together with polymerase and nucleotides. The nucleotides contain a small proportion of labeled nucleotides (labeled dUTP), which allows us to label the captured DNA and later subject it to flow cytometry for isolation.

Saturation of Beads with Biotinylated P1:

Biotinylated P1 is added to all isolated beads to saturate the beads with immobilized P1. All beads are isolated, and the leftovers are removed.

Clonal Amplification on Microfluidic Chambers:

The microfluidic chambers will be filled with isolated beads. Anti-P1 primer is added together with the PCR solution and cycles of amplification are performed to extend all P1 primers. After amplification, all the left-over substrates are removed and beads are treated with alkali to remove the non-biotinylated strand. Anti-P1 may then be added to perform, e.g., Pyrosequencing.

Sepharose beads can also be used instead of magnetic beads. In certain embodiments of the invention, Streptavidin-coated Sepharose beads may be used. For example, Sepharose beads that can be used include version 1.1 of the integrated chip on a PCR machine from MJ Research. The well geometry of this platform is similar to the one from 454 Corporation (Leamon and al., 2003). For clonal amplification using magnetic beads, version 1.2 of the integrated chip may be used, which has almost 6 times smaller wells. The same PCR conditions can be applied.

Clonal Amplification Using Plasmid DNA:

In certain embodiments, the methods of the invention may additionally be applied to a plasmid that is chopped with a shearing machine to 100-nucleotide long DNA. The shearing machine provides very homogenous fragment size down to 50 bases. The chopped plasmid DNA will be ligated to adapters and gel purified. Subsequently fragments will be cloned onto 30 μm Streptavidin-coated Sepharose beads and the above-mentioned process will be followed. The beads will then be loaded into the microfluidic chip with 35 μm well sizes bundled with the 128-feature CMOS chip. Clonally amplified DNA on beads will be subjected to complete extension having all four nucleotides present with all Pyrosequencing reagents. The efficiency will be measured by quantifying the light signal generated from Pyrosequencing extension reaction. The clonal amplification strategy of the present invention may be applied to different lengths of DNA fragments up to 2000 nucleotides long. After clonal amplification, cyclic Pyrosequencing can be performed to deduce the sequence and assemble plasmid DNA. This step will indicate the predicted coverage in sequencing that is enough for accurate sequence determination. In addition, the efficiency of clonal amplification can be monitored and PCR performed in designed format.

Development of Assembly Methodology and Software

Assembly:

The Pyrosequencing array will produce a large number of reads, each of which is prefixed by a pentamer that uniquely identifies the BAC clone source of the read within the array. With this information the reads can be separated into separate "clones". A whole-genome assembly methodology may comprise the following:

(1): Assemble the reads from each clone separately to obtain a set of contigs per clone. (2): Identify all pairwise overlaps between clone assemblies; filter out ones likely to be repeat-induced and obtain a set of unique overlaps. (3): Construct the overlap graph of contigs in clone assemblies, and perform sequencing-error correction. (4): Merge and extend contigs using the overlap graph, and use a merge operation between adjacent clones for further repeat resolution.

The principle of the subject methodology is that within short windows, the majority of the genome contains few or no high fidelity repeats that are longer than one read length. Therefore, sufficient shotgun sequencing from within the window will lead to a correct and gap-free assembly. To cluster reads within short windows, the following strategy may be followed: (A) in (1) above, reads are clustered within windows of one clone length; (1) will lead to reasonably contiguous assemblies of the majority of a mammalian genome. (B) In (4), reads are clustered into even shorter windows defined by successive BAC clone ends. The quality of assembly produced by the above procedure will depend on the following key parameters: the depth of clone coverage of the genome, the depth of shotgun sequence coverage of each clone, the read length, and the sequencing error rate. To assess assembly quality, computational simulations of sequencing may be performed as well as assembling genomes of varying size and repeat content and under different parameter settings. To develop such an assembly technique, Arachne (Batzoglou et al., 2002; Batzoglou et al., 2000; Jaffe et al., 2003) may be used as a module. Arachne is publicly available in source code and has been used successfully to assemble several genomes including the mouse (Mouse Genome Sequencing Consortium 2002).

The subject invention can also be used for expression or RNA profiling. For example, total RNA molecules can be extracted from a sample, such as a bacterial sample. Biotinylated oligo dT primers or biotinylated random hexamers are used to amplify the RNA molecules. In certain embodiments, biotinylated random pentamers, heptamers, or octamers may be used. After amplification, the cDNA molecules are immobilized on a solid support. Enzymatic restriction can be performed to generate overhang ends onto which an adapter can be ligated. For multiplex analysis, different samples may be ligated with adapters containing a unique tag, such as a nucleic acid barcode as described herein. The fragments are then detached and the same process for clonal amplification can be performed as for genome sequencing as described above. In certain embodiments, the subject invention relates to a method of clonal amplification for nucleic acid isolated from a bacterial sample. For example, described herein is a strategy to clonally amplify a unique bacterial nucleic acid on a solid surface such as magnetic beads.

Figure 2:
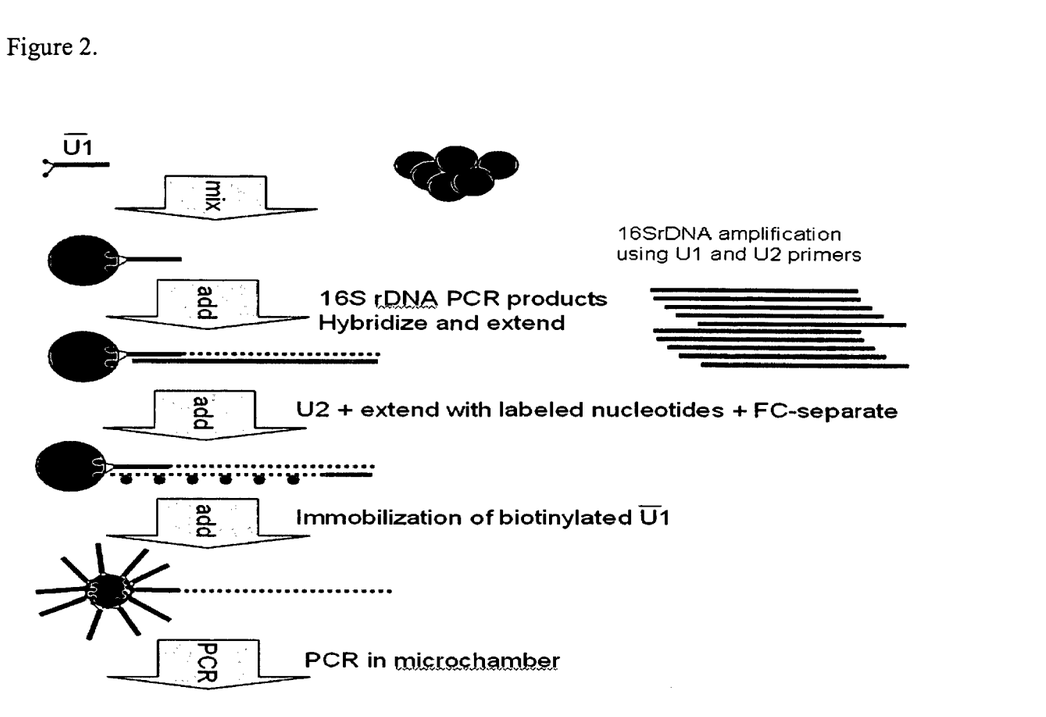
FIG. 2 is a schematic relating to clonal amplification.

Preparation of Beads Carrying Single U1-Bar Molecule:

U1-BAR is a 30-base long general oligonucleotide having two biotin molecules at the 5' end. Two biotin molecules permit efficient immobilization and also allow use of a higher temperature without being detached from the streptavidin molecule (Dressman et al., 2003). The ratio of magnetic beads to U1-BAR primers is designed to be large so that most beads that capture a primer molecule will capture exactly one. The solution will be saturated with fluorescent labeled U1 (seen as U1-BAR bar in FIG. 2), which will allow isolation of all beads carrying U1-BAR and recycling of the remaining beads.

Preparation of 16S rDNA for Clonal Amplification:

Sample containing isolated bacterial DNA from flora will be used for amplification using U1 and U2 universal primers U1 5'-AGAGTTTGATIITGGCTCAG-3' (SEQ ID NO: 2) (*E. coli* positions 8 through 27, International Union of Biochemistry nomenclature) and U2 5'-CGGITACCTTGTTAC-GACTT-3' (SEQ ID NO: 3) (*Escherichia coli* positions 1493 through 1513), respectively. These primers amplify 97% of all bacteria available in the databases. Most of the remaining 3% of bacteria are ones living in environments such as high salt, hot spring water, etc.

Single Molecule Capture of 16S rDNA on Bead and Extension:

Since the beads selected previously have a single attached U1-BAR primer, they can only capture a single DNA fragment. Therefore, the beads are saturated with denatured 16S rDNA amplicons for hybridization overnight. After ten extension cycles using U2-bar, all the magnetic beads are isolated and washed.

Labeling of Captured DNA:

Isolated beads from the previous step will be treated with alkali to denature the DNA and then the supernatant is removed. Anti-U2-BAR is added together with polymerase and nucleotides. The nucleotides contain a small proportion of labeled nucleotides (labeled dUTP), which allow labeling the captured DNA and later subjecting it to flow cytometry for isolation.

Saturation of Beads with Biotinylated U1-BAR:

Biotinylated U1-BAR is added to all isolated beads to saturate the beads with immobilized U1-BAR. All beads are isolated and the leftovers are removed.

Clonal Amplification on Microfluidic Chambers:

The microfluidic chambers will be filled with isolated beads. U2-bar primer is added together with the PCR solution and cycles of amplification are performed to extend all U1-BAR primers. After amplification, all the left-over substrates are removed and beads are treated with alkali to remove the non-biotinylated strand. U2-bar is added to perform Pyrosequencing to generate signature sequences of different bacteria.

REFERENCES

Bains, W. and Smith, G. C. (1988) A novel method for nucleic acid sequence determination. Journal of Theoretical Biology 135(3), 303-7.

Batzoglou, S., Jaffe, D. B., Stanley, K., Butler, J., Gnerre, S., Mauceli, E., Berger, B., Mesirov, J. P. and Lander, E. S. (2002) ARACHNE: a whole-genome shotgun assembler. Genome Res 12(1), 177-89.

Batzoglou, S., Pachter, L., Mesirov, J. P., Berger, B. and Lander, E. S. (2000) Human and mouse gene structure: comparative analysis and application to exon prediction. Genome Res 10(7), 950-8.

Braslavsky, I., Hebert, B., Kartalov, E. and Quake, S. R. (2003) Sequence information can be obtained from single DNA molecules. Proc Natl Acad Sci USA 100(7), 3960-4.

Brenner, S., Johnson, M., Bridgham, J., Golda, G., Lloyd, D., Johnson, D., Luo, S., McCurdy, S., Foy, M., Ewan, M., Roth, R., George, D., Eletr, S., Albrecht, G., Vermaas, E., Williams, S., Moon, K., Burcham, T., Pallas, M., DuBridge, R., Kirchner, J., Fearon, K., Mao, J. and Corcoran, K. (2000a) Gene expression analysis by massively parallel signature sequencing (MPSS) on microbead arrays. Nat Biotechnol 18(6), 630-634.

Brenner, S., Williams, S. R., Vermaas, E. H., Storck, T., Moon, K., McCollum, C., Mao, J. I., Luo, S., Kirchner, J. J., Eletr, S., DuBridge, R. B., Burcham, T. and Albrecht, G. (2000b) In vitro cloning of complex mixtures of DNA on microbeads: physical separation of differentially expressed cDNAs. Proc. Natl. Acad. Sci. USA. 97(4), 1665-70.

Collins, F. S., Morgan, M. and Patrinos, A. (2003) The human genome project: lessons from large-scale biology. Science 300, 286-290.

Deamer, D. W. and Akeson, M. (2000) Nanopores and nucleic acids: prospects for ultrarapid sequencing. Trends Biotechnol 18, 147-151.

Deamer, D. W. and Branton, D. (2002) Characterization of nucleic acids by nanopore analysis. Acc Chem Res 35, 817-825.

Dressman, D., Yan, H., Traverso, G., Kinzler, K. W. and Vogelstein, B. (2003) Transforming single DNA molecules into fluorescent magnetic particles for detection and enumeration of genetic variations. Proc Natl Acad Sci USA 100, 8817-8822.

Drmanac, R. and al., e. (2001) DNA sequencing by hybridization with arrays of samples or probes. Methods Mol Biol 170, 173-179.

Drmanac, S. (1998) Accurate sequencing by hybridization for DNA diagnostics and individual genomics. Nature Biotechnology 16, 54-58.

Elahi, E., Kumm, J. and Ronaghi, M. (2004) Global genetic analysis. J Biochem Mol Biol 37(1), 11-27.

Emrich, C. A., Tian, H., Medintz, I. L. and Mathies, R. A. (2002) Microfabricated 384-lane capillary array electrophoresis bioanalyzer for ultrahigh-throughput genetic analysis. Anal. Chem. 74, 5076-5083.

Fodor, S. P. A., Read, J. L., Pirrung, M. C., Stryer, L., Lu, A. T. and Solas, D. (1995) Light-directed, spatially addressable parallel chemical synthesis. Science 251(4995), 767-773.

Jaffe, D. B., Butler, J., Gnerre, S., Mauceli, E., Lindblad-Toh, K., Mesirov, J. P., Zody, M. and Lander, E. S. (2003) Whole-Genome Sequence Assembly for Mammalian Genomes: Arachne 2. Genome Res 13, 91-96.

Koutny, L. and Al., E. (2000) Eight hundred-base sequencing in a microfabricated electrophoretic device. Anal. Chem. 72, 2288-3391.

Leamon, J. H. and al., e. (2003) A massively parallel PicoTiterPlate based platform for discrete picoliter-scale polymerase chain reactions. Electrophoresis 24, 3769-3777.

Levene, M. J. and al., e. (2003) Zero-mode waveguides for single-molecule analysis at high concentrations. Science 299, 682-686.

Li, J., Gershow, M., Stein, D., Brandin, E. and Golovchenko, J. A. (2003) DNA molecules and configurations in a solid-state nanopore microscope. Nat Mater 2, 611-615.

Lipshutz, R. J. and al., e. (1995) Using oligonucleotide probe arrays to access genetic diversity. Biotechniques 19, 442-447.

Metzker, M. L., Raghavachari, R., Richards, S., Jacutin, S. E., Civitello, A., Burgess, K. and Gibbs, R. A. (1994) Termination of DNA synthesis by novel 3'-modified-deoxyribonucleoside 5'-triphosphates. Nucleic Acids Research 22(20), 4259-67.

Mitra, R. D., Butty, V. L., Shendure, J., Williams, B. R., Housman, D. E. and Church, G. M. (2003) Digital genotyping and haplotyping with polymerase colonies. Proc Natl Acad Sci USA 100(10), 5926-31.

Mitra, R. D. and Church, G. M. (1999) In situ localized amplification and contact replication of many individual DNA molecules. Nucleic Acids Res 27, 1-6.

Paegel, B. M., Blazej, R. G. and Mathies, R. A. (2003) Microfluidic devices for DNA sequencing: sample preparation and electrophoretic analysis. Curr Opin Biotechnol 14, 42-50.

Patil, N., Berno, A. J., Hinds, D. A., Barrett, W. A., Doshi, J. M., Hacker, C. R., Kautzer, C. R., Lee, D. H., Marjoribanks, C., McDonough, D. P., Nguyen, B. T., Norris, M. C., Sheehan, J. B., Shen, N., Stem, D., Stokowski, R. P., Thomas, M. O., Trulson, M. O., Vyas, K. R., Frazer, K. A., Fodor, S. P. and Cox, D. R. (2001) Blocks of limited haplotype diversity revealed by high-resolution scanning of human chromosome 21. Science 294(5547), 1719-23.

Ronaghi, M. (1998) Pyrosequencing: a tool for sequence-based DNA analysis. Doctoral thesis ISBN 91-7170-297-0.

Ronaghi, M. (2001) Pyrosequencing sheds light on DNA sequencing. Genome Res 11(1), 3-11.

Ronaghi, M. (2003) Pyrosequencing for SNP genotyping. Methods Mol Biol 212, 189-195.

Ronaghi, M. and Elahi, E. (2002) Pyrosequencing for microbial typing. J Chromatogr B Analyt Technol Biomed Life Sci. 782, 67-72.

Ronaghi, M., Karamohamed, S., Pettersson, B., Uhlen, M. and Nyren, P. (1996) Real-time DNA sequencing using detection of pyrophosphate release. Analytical Biochemistry 242(1), 84-9.

Ronaghi, M., Nygren, M., Lundeberg, J. and Nyren, P. (1999) Analyses of secondary structures in DNA by pyrosequencing. Analytical Biochemistry 267(1), 65-71.

Ronaghi, M., Uhlen, M. and Nyren, P. (1998) A sequencing method based on real-time pyrophosphate. Science 281 (5375), 363.

Sanger, F., Nicklen, S. and Coulson, A. R. (1977) DNA sequencing with chain-terminating inhibitors. Proc. Natl. Acad. Sci. USA. 74(12), 5463-7.

Sarkis, G. and al., e. (2003) Sequence analysis of the pAdEasy-1 recombinant adenoviral construct using the 454 Life Sciences sequencing-by-synthesis method. NCBI AY370911, gi:34014919.

the present application, including any definitions herein, will control.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: P1 primer

<400> SEQUENCE: 1 tttttttgc aaatgttatc gaggtccggc                                      30

<210> SEQ ID NO 2
<211> LENGTH: 20
<212> TYPE: DNA
<213> ORGANISM: Artificial Sequence
<220> FEATURE:
<223> OTHER INFORMATION: U1 primer
<220> FEATURE:
<221> NAME/KEY: misc_feature
<222> LOCATION: 11, 12
<223> OTHER INFORMATION: n = inosine

<400> SEQUENCE: 2
agagtttgat nntggctcag                                                20

<210> SEQ ID NO 3
<211> LENGTH: 20
<212> TYPE: DNA
<213> ORGANISM: Artificial Sequence
<220> FEATURE:
<223> OTHER INFORMATION: U2 primer
<220> FEATURE:
<221> NAME/KEY: misc_feature
<222> LOCATION: 4
<223> OTHER INFORMATION: n = inosine

<400> SEQUENCE: 3
cggntacctt gttacgactt                                                20
```

Southern, E. M. (1989) Analysing polynucleotide sequences. Patent WO/10977.

Williams, J. (2001) Heterogenous assay for pyrophosphate, U.S. Pat. No. 6,306,607, USA.

Winters-Hilt, S. and al., e. (2003) Accurate classification of basepairs on termini of single DNA molecules. Biochys J 84, 967-976.

INCORPORATION BY REFERENCE

All publications and patents mentioned herein are hereby incorporated by reference in their entirety as if each individual publication or patent was specifically and individually indicated to be incorporated by reference. In case of conflict,

What is claimed is:

1. A method of labeling and amplifying a nucleic acid molecule in a plurality of nucleic acid molecules, comprising the steps of:
    (a) attaching a unique antiprimer $\overline{P1}$ to each of a plurality of nucleic acid molecules to be amplified;
    (b) hybridizing a molecule from step (a) to a solid surface in a plurality of solid surfaces, wherein each of said solid surfaces is attached to a single molecule of primer P1, which is complementary to the unique antiprimer $\overline{P1}$, to form a single captured DNA fragment on each solid surface;
    (c) extending P1 hybridized in step (b) to form a double stranded fragment, then denaturing the double stranded fragment to form a single stranded captured DNA fragment attached to each solid surface through primer P1;

(d) labeling the single stranded captured DNA fragment from step (c) by nucleotide extension;

(e) isolating the captured DNA fragment labeled in step (d) by the label;

(f) attaching additional primers P1 to the solid surface after isolating the labeled, captured DNA fragment from step (e); and (g) amplifying the captured DNA fragment from step (e) using the additional primers attached in step (f).

2. The method of claim 1, wherein the unique antiprimer $\overline{P1}$ is an adapter comprising a unique barcode, the method further comprising a step of sequencing the amplified nucleic acid molecules and identifying the barcode sequence.

3. The method of claim 2, wherein the unique antiprimer $\overline{P1}$ is attached to the nucleic acid molecule by ligating the adapter comprising a unique barcode to the nucleic acid molecule.

4. The method of claim 2, wherein the unique barcode comprises a unique sequence of five nucleotides.

5. The method of claim 1, wherein the unique antiprimer identifies a source of nucleic acid.

6. The method of claim 2, wherein the unique barcode identifies a source of nucleic acid.

7. The method of claim 5 or claim 6, wherein the source of nucleic acid is selected from the group consisting of: a BAG clone, a bacterium, and a tissue sample.

8. The method of claim 1, wherein the labeled nucleic acid molecule is amplified by a sequencing-by-synthesis method.

9. The method of claim 8, wherein the labeled nucleic acid molecule is amplified by a method selected from the group consisting of: massively parallel signature sequencing, BEAM, and polony technology.

10. A method of clonal amplification of a nucleic acid molecule, comprising the steps of:

(a) labeling the nucleic acid molecule with a unique anti primer $\overline{P1}$;

(b) hybridizing said nucleic acid molecule containing antiprimer $\overline{P1}$ to one primer P1 molecule, where only one primer P1 molecule is immobilized on a solid surface;

(c) incubating the solid surface of (b) comprising P1 and nucleic acid molecule containing antiprimer $\overline{P1}$ with polymerase and nucleotides under conditions permitting extension of said one molecule of immobilized primer P1 to form a double stranded fragment complementary to the nucleic acid molecule containing antiprimer $\overline{P1}$, then denaturing the double stranded fragment to form a single stranded captured DNA fragment attached to each solid surface through primer P1;

(d) labeling the single stranded captured DNA fragment from step (c);

(e) isolating a solid surface containing labeled product from step (d) from solid surfaces not containing labeled product;

(f) incubating the isolated solid surface of (e) under conditions permitting denaturing of the nucleic acid molecules containing antiprimers $\overline{P1}$ from the extended primers P1; removing supernatant containing extended anti-primers as a result of the denaturing; incubating the solid surface under conditions permitting immobilizing of additional primers P1 on the solid surface; and (g) incubating the solid surfaces of (f) with polymerase, nucleotides, and one or more oligonucleotides that hybridize to the immobilized anti-primers of (f), under conditions permitting extension of said hybridized oligonucleotides, wherein the nucleic acid molecule is thereby amplified.

11. The method of claim 10, wherein the unique anti primer of (a) is an adapter comprising a unique barcode the method further comprising a step of sequencing the amplified nucleic acid molecules and identifying the barcode sequence.

12. The method of claim 11, wherein the unique barcode comprises a unique sequence of five nucleotides.

13. The method of claim 10, further comprising: (g) sequencing the immobilized amplified nucleic acid molecules of (f).

14. The method of claim 13, wherein the nucleic acid molecules are sequenced by pyrosequencing.

15. The method of claim 10, wherein the unique antiprimer identifies a source of nucleic acid.

16. The method of claim 11, wherein the unique barcode identifies a source of nucleic acid.

17. The method of claim 15 or claim 16, wherein the source of nucleic acid is selected from the group consisting of: a BAG clone, a bacterium, and a tissue sample.

18. The method of claim 10, wherein the solid surface is a bead.

19. The method of claim 18, wherein the bead is selected from the group consisting of: a magnetic bead and a Sepharose bead.

* * * * *

UNITED STATES PATENT AND TRADEMARK OFFICE
CERTIFICATE OF CORRECTION

PATENT NO. : 7,622,281 B2
APPLICATION NO. : 11/134683
DATED : November 24, 2009
INVENTOR(S) : Mostafa Ronaghi and Foad Mashayekhi

It is certified that error appears in the above-identified patent and that said Letters Patent is hereby corrected as shown below:

Claim 7, line 24: currently reads "nucleic acid is selected from the group consisting of: a BAG"

should read: "nucleic acid is selected from the group consisting of: a BAC"

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,622,281 B2
APPLICATION NO. : 11/134683
DATED : November 24, 2009
INVENTOR(S) : Mostafa Ronaghi and Foad Mashayekhi It is certified that error appears in the above-identified patent and that said Letters Patent is hereby corrected as shown below:

Column 15, Claim 7, line 24: currently reads "nucleic acid is selected from the group consisting of: a BAG"

should read: "nucleic acid is selected from the group consisting of: a BAC"

This certificate supersedes the Certificate of Correction issued May 25, 2010.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,622,281 B2  
APPLICATION NO. : 11/134683  
DATED : November 24, 2009  
INVENTOR(S) : Mostafa Ronaghi

It is certified that error appears in the above-identified patent and that said Letters Patent is hereby corrected as shown below:

Title Page, Item [*]

Delete the phrase "by 244 days" and insert -- by 246 days --.

Signed and Sealed this

Twenty-fourth Day of August, 2010

David J. Kappos  
*Director of the United States Patent and Trademark Office*